US010322030B1

(12) United States Patent
Al Sabti (10) Patent No.: US 10,322,030 B1
(45) Date of Patent: Jun. 18, 2019

(54) INFUSION CANNULA SYSTEM FOR PARS PLANA VITRECTOMY

(71) Applicant: Khalid Al Sabti, Mubarak Al Abdulla (KW)

(72) Inventor: Khalid Al Sabti, Mubarak Al Abdulla (KW)

(*) Notice: Subject to any disclaimer, the term of this patent is extended or adjusted under 35 U.S.C. 154(b) by 0 days.

(21) Appl. No.: 16/189,883

(22) Filed: Nov. 13, 2018

(51) Int. Cl.
*A61F 9/007* (2006.01)
*A61B 17/34* (2006.01)

(52) U.S. Cl.
CPC ...... *A61F 9/00736* (2013.01); *A61B 17/3421* (2013.01); *A61B 17/3462* (2013.01)

(58) Field of Classification Search
CPC ...... A61F 9/013; A61F 9/007; A61F 9/00727; A61F 9/00709; A61F 9/0026; A61F 9/0008; A61F 9/00736; A61B 17/0469; A61B 17/3421; A61B 17/3462
See application file for complete search history.

(56) References Cited

U.S. PATENT DOCUMENTS

| 5,192,293 A | 3/1993 | Cartwright |
| 5,690,658 A | 11/1997 | McAdams |
| 5,743,916 A | 4/1998 | Greenberg |
| 5,882,344 A | 3/1999 | Stouder, Jr. |
| 2012/0191064 A1* | 7/2012 | Conston ............ A61F 9/00727 604/506 |
| 2017/0266045 A1* | 9/2017 | Kangastupa ......... A61F 9/0026 |

FOREIGN PATENT DOCUMENTS

| CN | 201542739 U | 8/2010 |
| JP | 2007319423 A | 12/2007 |

* cited by examiner

*Primary Examiner* — Edelmira Bosques
*Assistant Examiner* — Hamza A Darb
(74) *Attorney, Agent, or Firm* — Richard C. Litman (57) ABSTRACT

The infusion cannula system for pars plana vitrectomy includes a port (100) mounted over a sclerotomy on the patient's eye (200) and an infusion cannula assembly (400) adapted for connection to a vitrectomy machine that maintains pressure in the eye during the procedure. The port (100) includes an external cylindrical shell (10) that is kept stationary and an internal hub (14) having an insertion tube (17) extending therefrom. The internal hub (14) is threadable into the cylindrical shell (10) in increments to control the depth of penetration of the insertion tube (17) through the sclerotomy incision into the vitreous cavity. The infusion cannula (25) is introduced into the eye (200) through the insertion tube (17) to the desired depth. The internal hub (14) may have a pointer (15) that points to calibration indicia on the cylindrical shell (10) corresponding to the depth of insertion of the infusion cannula (25).

17 Claims, 7 Drawing Sheets

INFUSION CANNULA SYSTEM FOR PARS PLANA VITRECTOMY

BACKGROUND

1. Field

The disclosure of the present patent application relates to ocular surgery, and particularly to an infusion cannula system for pars plana vitrectomy.

2. Description of the Related Art

Pars plana Vitrectomy (PPV), or simply vitrectomy, is a microsurgical procedure frequently performed by retina surgeons to surgically treat various retina conditions requiring the introduction of fine delicate microsurgical instruments within the eye. It is the second-most frequently performed procedure, after cataract surgery. In recent years, these delicate instruments have gone a long way towards better performance through continuous research and instrument development.

During vitrectomy, the vitreous gel is removed by an instrument called the vitreous cutter and is replaced by a balanced salt solution (BSS) to maintain the ocular pressure and structure. Typically three sclerotomies are performed, one inferiorly for an infusion cannula and two superiorly for a light and for insertion of instruments, such as a cutter, forceps, etc. The balanced salt solution is injected into the vitreous cavity by the infusion cannula system, which is controlled by the vitrectomy machine that maintains eye pressure within normal range throughout the surgery. It is very crucial that the infused solution is injected into the vitreous cavity, and in cases in which this fluid is not injected into the vitreous cavity, serious complications are likely to occur.

It is the responsibility of the surgeon to ensure that the inner part of the infusion cannula is placed well within the vitreous cavity (by visually looking at the tip of the inner side of the cannula) before initiating the flow of balanced solution. The existing infusion cannula system often has a standard length extending inside the eye, which is either 4 or 6 mm. The 4 mm length is the most commonly used and is sufficient for most cases. However, in some cases, as in undilated pupil, hazy media, and complex retinal detachments (as in trauma), it may be very difficult to ensure that the inner part of the cannula is within the vitreous cavity, and thus longer cannulas are required to ensure correct placement. On the other hand, some cases require shorter cannulas, as a 4 mm cannula might be too long and may cause damage to the natural lens of a small eye in a premature baby.

Therefore, the standard 4 mm cannula is not acceptable for all cases since some eyes need longer cannulas, while others require shorter infusion cannulas for safer surgery. Thus, an infusion cannula system for pars plana vitrectomy solving the aforementioned problems is desired.

SUMMARY

The infusion cannula system for pars plana vitrectomy includes a port mounted over a sclerotomy on the patient's eye and an infusion cannula adapted for connection to a vitrectomy machine that maintains pressure in the eye during the procedure. The port includes an external cylindrical shell that is kept stationary and an internal hub having an insertion tube extending therefrom. The internal hub is threadable into the cylindrical shell in increments to control the depth of penetration of the insertion tube through the sclerotomy incision into the vitreous cavity. The infusion cannula is introduced into the eye through the insertion tube to the desired depth. The internal hub may have a pointer that points to calibration indicia on the face of the cylindrical shell corresponding to the depth of insertion of the infusion cannula.

A trocar is used to install the insertion tube into the eye. The distal end of the trocar handle and the distal end of the infusion cannula handle may have pins extending therefrom that releasably snap into the opening of the lumen on the face of the internal hub or in recesses at opposite ends thereof so that the surgeon may rotate the internal hub to adjust the depth of insertion of the infusion cannula either during installation of the port or during installation of the infusion cannula. The cylindrical shell may have wings or ribs extending radially therefrom so that the shell may be held stationary as the internal hub is rotated. Preferably, the present system permits the infusion cannula to be inserted into the eye to any depth in the range of three millimeters through seven millimeters.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The port 100 of an infusion cannula system for pars plana vitrectomy is shown in FIGS. 1A-3B as it would be used during a pars plana vitrectomy procedure. As seen in the aforementioned drawings, an outer or external cylindrical shell 10 or socket of the port 100 rests on the outer surface of the eye 200, and holds an internal hub 14 that has an insertion tube 17 extending into the vitreous chamber 202 of the eye 100. The internal hub 14 is adjustable in relation to the cylindrical shell 10 so the depth of the insertion tube 17 can be adjusted.

Figure 1A:
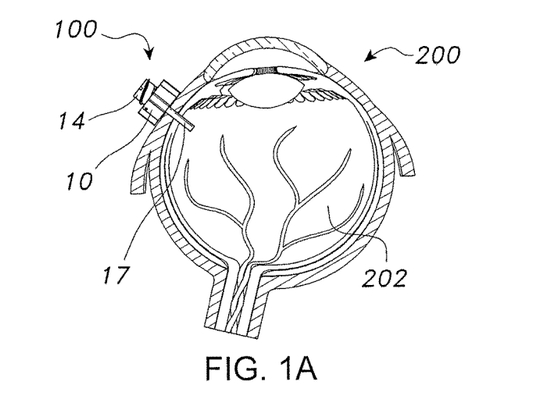
FIG. 1A is an environmental, perspective view of the port of an infusion cannula system for pars plana vitrectomy adjusted for a cannula depth of 3 mm.
Figure 1B:
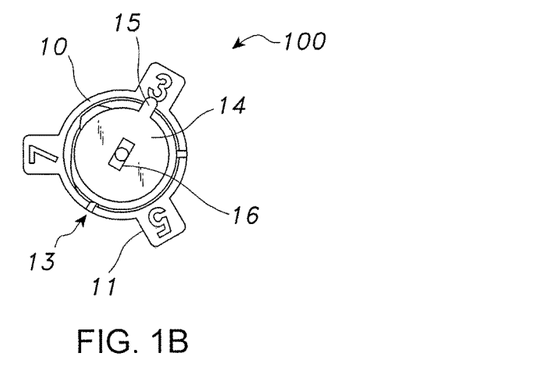
FIG. 1B is a top view of the port of the system of FIG. 1A, showing the corresponding face of the port.
Figure 2A:
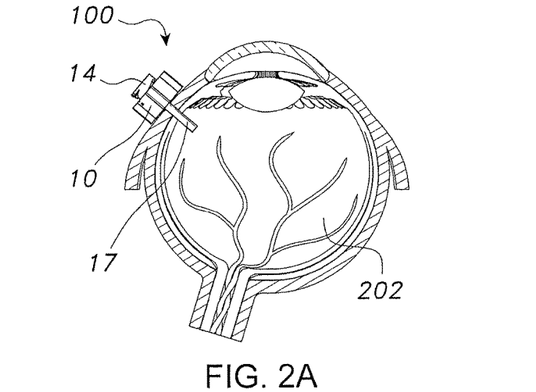
FIG. 2A is an environmental, perspective view of the port of an infusion cannula system for pars plana vitrectomy adjusted for a cannula depth of 5 mm.
Figure 2B:
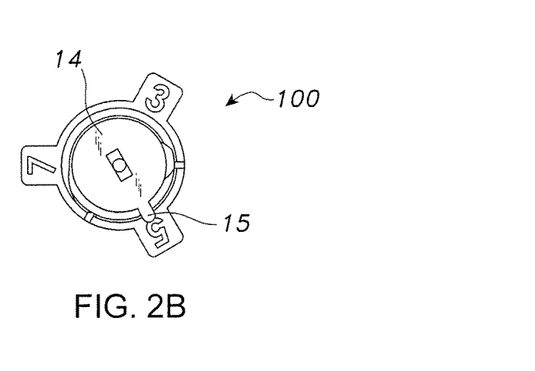
FIG. 2B is a top view of the port of the system of FIG. 2A, showing the corresponding face of the port.
Figure 3A:
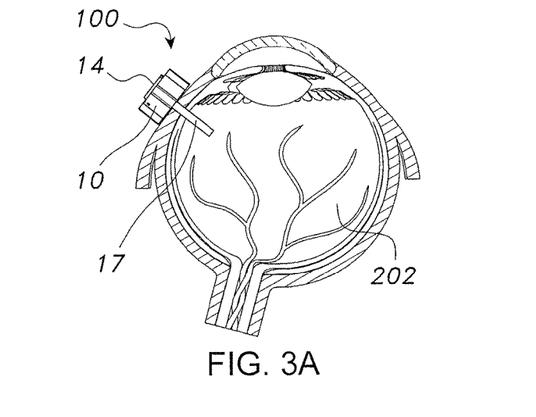
FIG. 3A is an environmental, perspective view of the port of an infusion cannula system for pars plana vitrectomy adjusted for a cannula depth of 7 mm.
Figure 3B:
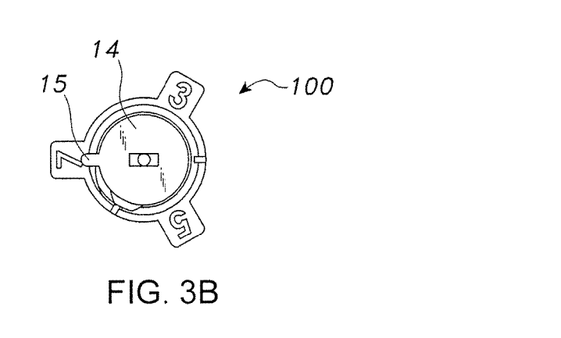
FIG. 3B is a top view of the port of the system of FIG. 3A, showing the corresponding face of the port.

FIGS. 1A and 1B show the port 100 at a minimal cannula depth setting. As seen in FIG. 1A, the insertion tube 17 is at a shallow depth due to the internal hub 14 extending out from the proximal end of the cylindrical shell 10. FIG. 1B shows a top view of the port 100 when set at the minimal depth. In FIG. 1B, the depth indicator pointer 15 on the internal hub 14 is aligned with indicia for the number "3" on the depth scale located on the proximal face of the cylindrical shell 10. This indicates that the insertion tube 17 set to at a depth of 3 millimeters (mm) below the distal end of the cylindrical shell 10. FIGS. 2A and 2B show the port 100 at a middle depth, where the insertion tube 17 extends slightly further into the eye 200. The pointer 15 is aligned with indicia for the number "5" on the depth scale, thus confirming the insertion tube 17 is at a depth of 5 mm. A maximum depth of the insertion tube 17 is shown in FIGS. 3A and 3B. In this position, the internal hub 14 barely extends out from the proximal end of the cylindrical shell 10, and the insertion tube 17 is at its deepest position. Similar to the previously described positions, the pointer 15 is aligned with indicia for the number "7" on the depth scale to indicate that the insertion tube 17 is at a depth of 7 mm from the distal end of the cylindrical shell 10.

Figure 4A:
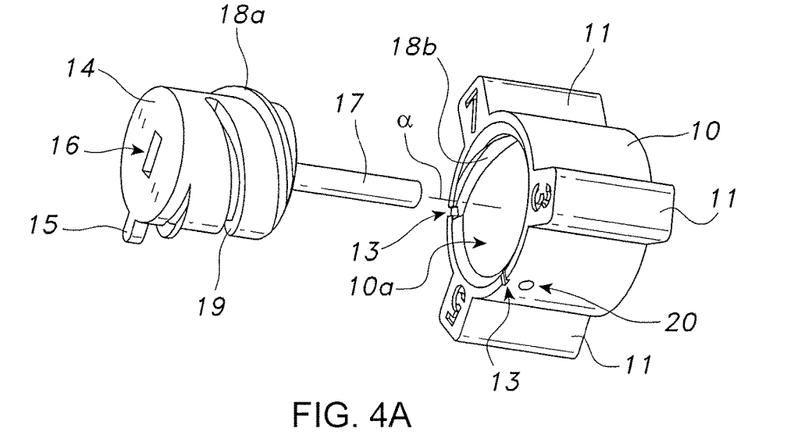
FIG. 4A is a partially exploded perspective view of the port of an infusion cannula system for pars plana vitrectomy, showing the internal hub exploded from the cylindrical shell.
Figure 4B:
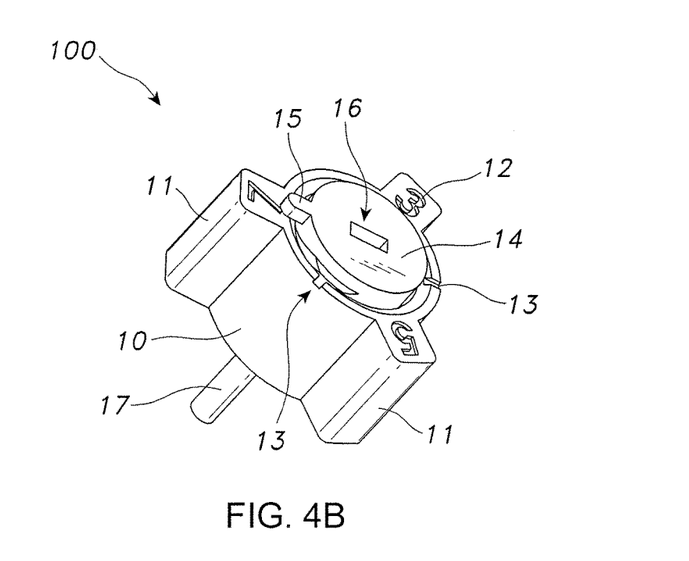
FIG. 4B is a perspective view of the port of an infusion cannula system for pars plana vitrectomy, shown adjusted for a cannula depth of 7 mm.

FIGS. 4A and 4B show the port 100 in separated and fully engaged configurations, respectively. As seen in FIG. 4A, the internal hub 14 includes a helical projection or external thread 18a and a helical channel 19 on an outer surface of the hub 14. The insertion tube 17 extends out from a center of the distal end of the hub 14. The lumen of the insertion tube is aligned with a lumen 16 that extends up through the hub 14 to the proximal face opposite the insertion tube 17. On the proximal face of the hub 14, the lumen 16 may have a rectangular opening for accepting the cannula and locking pins of a cannula or trocar handle for rotating the internal hub 14, or alternatively, the proximal face may have recesses at opposite ends of the lumen 16 for receiving the pins. The depth indicator pointer 15 extends out laterally from an upper edge of the hub 14.

The external thread 18a interacts with a helical groove or internal thread 18b defined in the cylindrical shell 10. Both the external thread 18a and internal thread 18b are pitched relative to the axis α of the cannula at an angle that will result in the desired vertical displacement of the insertion tube 17 per rotation. For example, in the embodiment shown in the drawings, where the insertion tube's 17 depth is adjustable from 3 mm to 7 mm over 240° of rotation, the external thread 18a and internal thread 18b will be pitched at an angle that drops 1 mm every 60° of rotation. The exact angle relative to a plane transverse to the axis α of the cannula will depend on the diameter of the bore 10a in the cylindrical shell 10. In a case where the diameter of the bore 10a is 10 mm, the angle would be roughly 11.6 degrees offset from a plane transverse to the axis α of the insertion tube 17.

The outer surface of the internal hub 14 also includes a helical channel 19 having the same pitch as the external thread 18a. A pin 20 extending into the bore 10a of the cylindrical shell 10 sits in the channel 19 when the device is in an assembled configuration. The interaction between the channel 19 and the pin 20 limits the rotation of the internal hub 14 in relation to the cylindrical shell 10. At maximum cannula depth, the pin 20 hits one end of the channel 19, and at minimum depth the pin 20 hits the opposite end of the channel 19. Therefore, the channel 19 prevents the internal hub 14 from being unscrewed out of the cylindrical shell 10, and also prevents the insertion tube 17 from being set to a depth past the maximum.

The cylindrical shell 10 includes a tubular body defining bore 10a. The tubular body has three evenly spaced external wings or ribs 11 extending down its length. Each wings or rib 11 may include a number or other identifier to indicate a depth of the insertion tube 17 to a user. In the embodiment shown in the drawings, the wings 11 include the numbers "3", "3", and "7", which refer to insertion tube 17 depth in mm. Between the "3" and "5" wings 11, and the "5" and "7" wings 11, the proximal end of the cylindrical shell 10 is notched 13 to indicate a midpoint, which would equate to a depth of 4 mm and 6 mm, respectively. As previously introduced, the inner surface of the bore 10a includes an internal thread 18b to accept the external thread 18a of the internal hub 14, as well as a pin 20 to sit within the helical channel 19 of the internal hub 14.

Figure 5A:
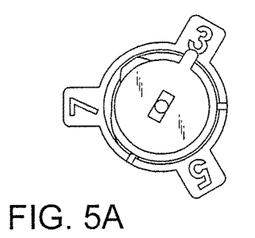
FIG. 5A is a top view of the port of an infusion cannula system for pars plana vitrectomy adjusted to a cannula depth of 3 mm.
Figure 5B:
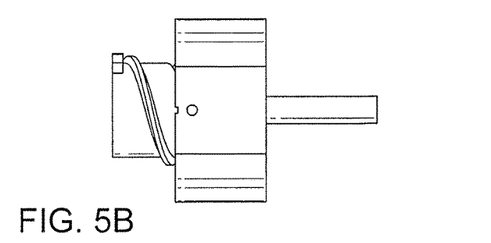
FIG. 5B is a side view of the port corresponding to the depth setting shown in FIG. 5A.
Figure 6A:
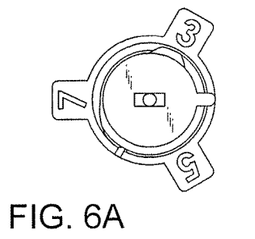
FIG. 6A is a top view of the port of an infusion cannula system for pars plana vitrectomy adjusted to a cannula depth of 4 mm.
Figure 6B:
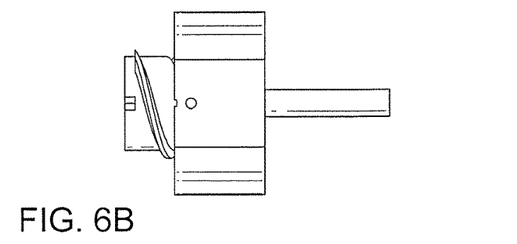
FIG. 6B is a side view of the port corresponding to the depth setting shown in FIG. 6A.
Figure 7A:
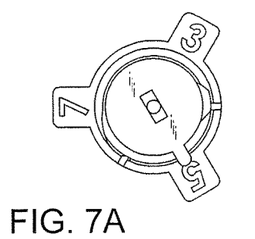
FIG. 7A is a top view of the port of an infusion cannula system for pars plana vitrectomy adjusted to a cannula depth of 5 mm.
Figure 7B:
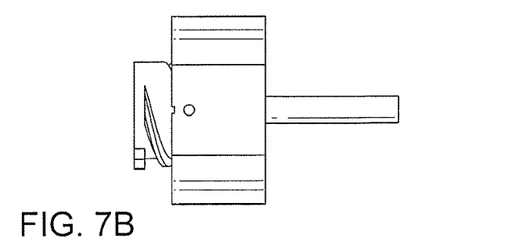
FIG. 7B is a side view of the port corresponding to the depth setting shown in FIG. 7A.
Figure 8A:
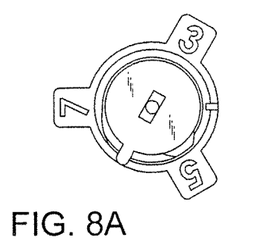
FIG. 8A is a top view of the port of an infusion cannula system for pars plana vitrectomy adjusted to a cannula depth of 6 mm.
Figure 8B:
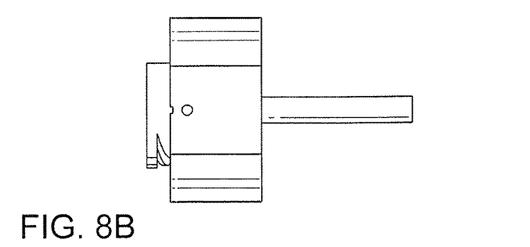
FIG. 8B is a side view of the port corresponding to the depth setting shown in FIG. 8A.
Figure 9A:
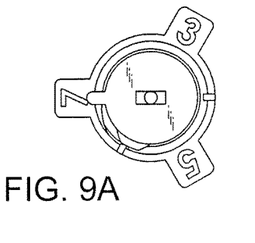
FIG. 9A is a top view of the port of an infusion cannula system for pars plana vitrectomy adjusted to a cannula depth of 7 mm.
Figure 9B:
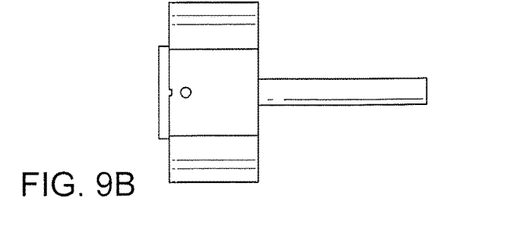
FIG. 9B is a side view of the port corresponding to the depth setting shown in FIG. 9A.

FIGS. 5A-9B show the progression resulting from adjusting the insertion tube 17 from a minimum depth, where the tube 17 extends 3 mm from the distal end of the cylindrical shell 10, to a maximum depth of 7 mm from the distal end of the cylindrical shell 10. FIGS. 5A and 5B show the device at an insertion tube depth of 3 mm; FIGS. 6A and 6B show the device at an insertion tube depth of 4 mm, FIGS. 7A and 7B show the device at an insertion tube depth of 5 mm, FIGS. 8A and 8B show the device at an insertion tube depth of 6 mm, and FIGS. 9A and 9B show the device at an insertion tube depth of 7 mm. As seen by the progression in FIGS. 5A-9B, movement of the depth indicator pointer 15 towards the higher numbers screws the internal hub 14 into the cylindrical shell 10, thereby moving the end of the insertion tube 17 further below the distal end of the cylindrical shell 10.

Figure 10A:
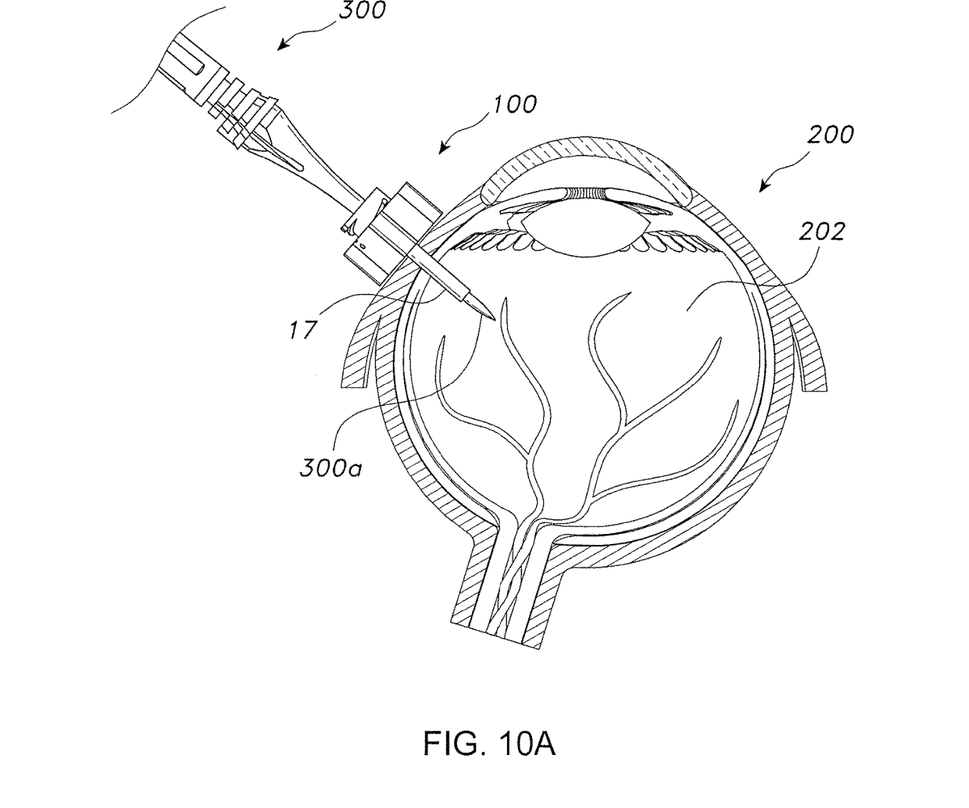
FIG. 10A is an environmental, perspective view of the port of an infusion cannula system for pars plana vitrectomy being installed with a trocar.
Figures 10B, 10C:
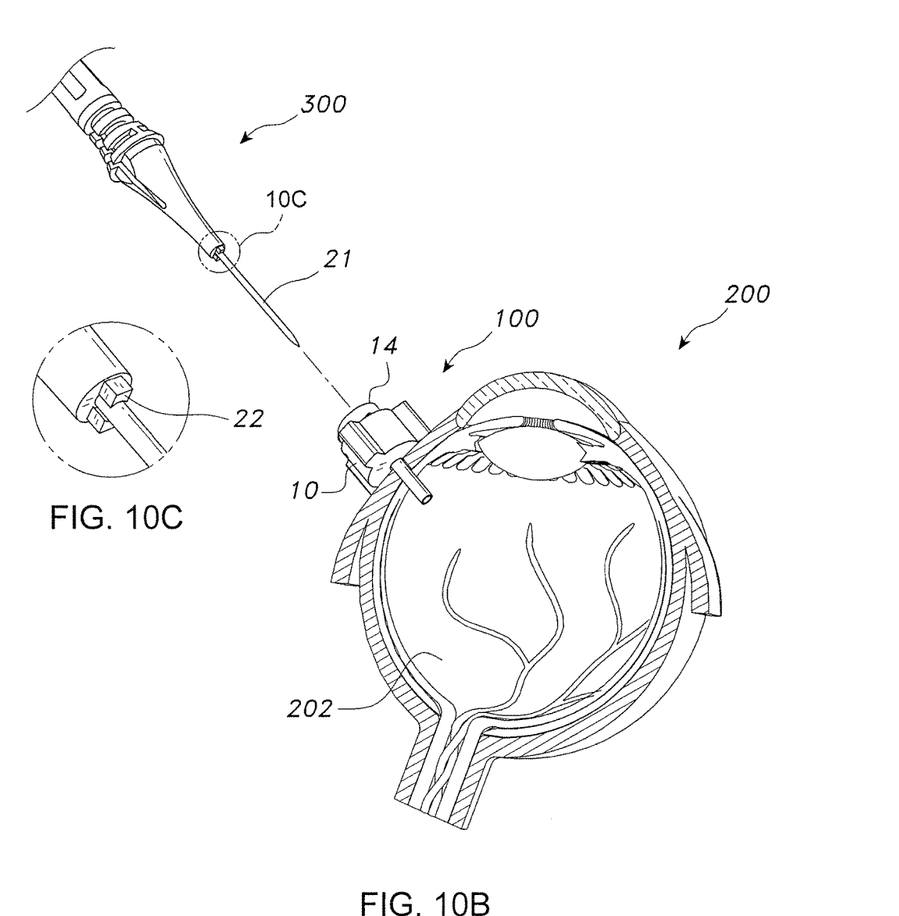
FIG. 10B is an exploded environmental, perspective view of a trocar being withdrawn from the port of an infusion cannula system for pars plana vitrectomy.
FIG. 10C is a detailed perspective view of the distal end of the trocar handle, showing pins that releasably engage the opening of the lumen in the face of the internal hub, or recesses at opposite ends thereof.

FIGS. 10A and 10B show the port 100 immediately after attachment to the eye 200. The insertion tube 17 is inserted into the eye 200 using a trocar 300 that has a needle 21 with its needle point depicted at 300a. The needle point 300a protrudes out from the end of the insertion tube 17 and is used to perforate the sclera so the insertion tube 17 can be inserted. Once the insertion tube 17 has been inserted into the vitreous chamber 202 of the eye, the trocar 300 and attached needle point 300a are removed, and the port 100 remains anchored in the eye 200 by the insertion tube 17, as seen in FIG. 4B.

The end of the handle of the trocar 300 from which the needle 300a extends may have pins 22 on opposing sides of the needle 300a, as seen in FIG. 10C. The pins 22 are sized and shaped to form a snap fit with the rectangular opening of the lumen 16 on the proximal face or end of the internal hub 14. When the pins 22 of the trocar 300 are mated with the rectangular opening of lumen 16, the trocar 300 can be used to rotate the internal hub 14 for setting the insertion tube 17 to a desired depth. This interaction will typically be used to adjust the depth of the insertion tube 17 before it has been inserted into the eye 200.

Figures 11A, 11B:
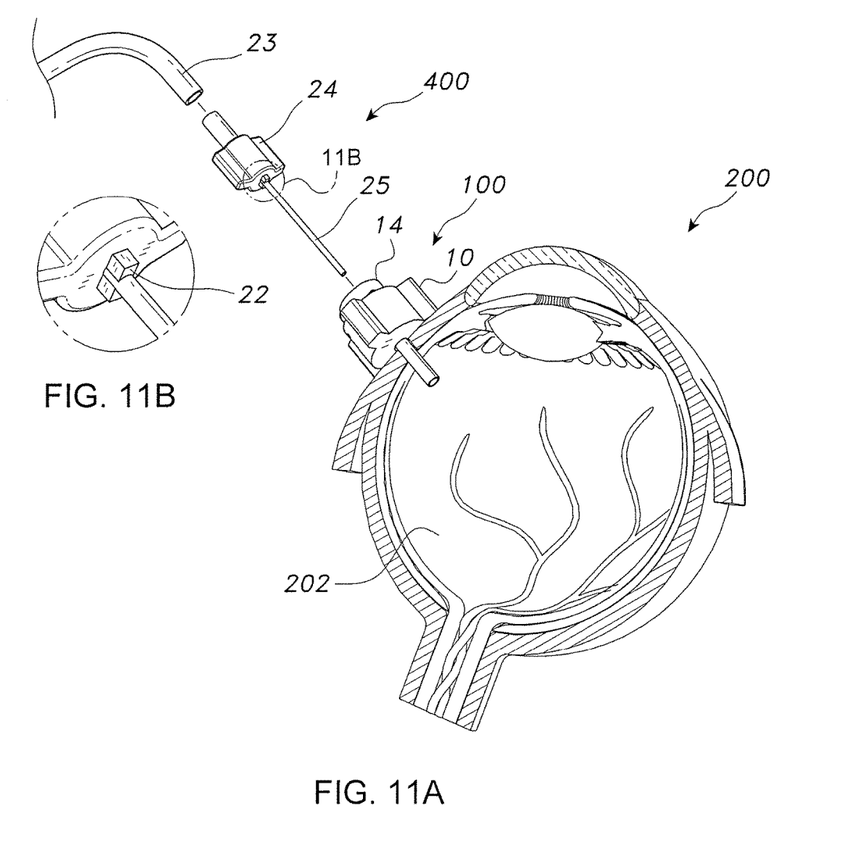
FIG. 11A is an exploded environmental perspective view of an infusion cannula system for pars plana vitrectomy, showing the infusion cannula and infusion tubing exploded from a port installed in the patient's eye.
FIG. 11B is a detailed perspective view of the distal end of the handle of the infusion cannula, showing the pins that releasably engage the opening of the lumen in the face of the internal hub, or recesses at opposite ends thereof.
Figure 11C:
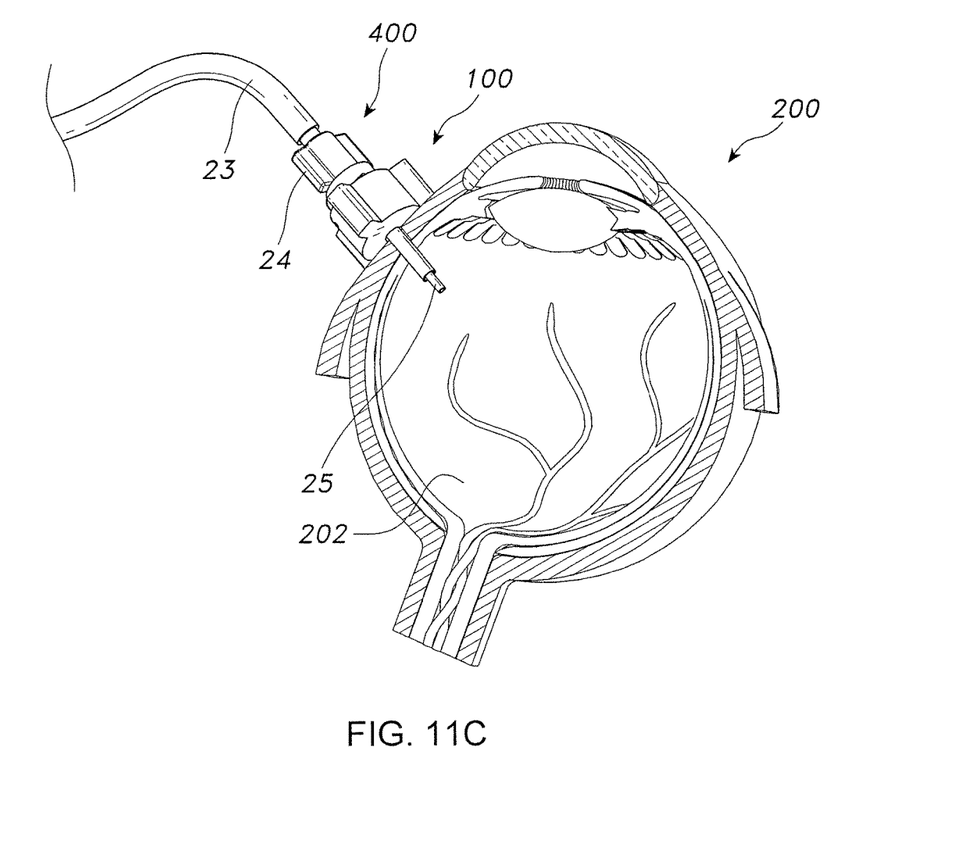
FIG. 11C shows an environmental perspective view of an infusion cannula system for pars plana vitrectomy attached to the patient's eye.

Once the port 100 is inserted into the eye 200, and the insertion tube 17 is set to a depth where its end is in the vitreous chamber 202 of the eye, an infusion cannula assembly 400 can be introduced, as seen in FIGS. 11A-11C. The assembly 400 includes an infusion cannula body or handle 24 attached to an infusion cannula 25. The infusion cannula 25 is dimensioned and configured to fit inside the insertion tube 17 of the port 100. The cannula body 24 may include pins 22, similar to the pins 22 of the trocar 300, which mate with the rectangular opening on the proximal face of the internal hub 14. The pins 22 allow a user to adjust the depth of the insertion tube 17, and hence the cannula 25, when the device is inserted in the eye by rotating the cannula body or handle 24, which has diametrically opposed wings or ribs extending therefrom for that purpose. An infusion tube 23 is attached to the cannula body 24 at the end opposite the infusion cannula 25. The infusion tube 23 is adapted for connection to a vitrectomy machine and is used to infuse new fluid into the eye.

A method for performing a pars plana vitrectomy includes adjusting a cannula depth through a port 100 having an internal hub 14 and cylindrical shell 10 by rotating the internal hub 14 relative to the cylindrical shell 10. Following the initial adjustment, a needle 300a attached to a trocar 300 is inserted into the insertion tube 17 with the needle 300a extending out from and end of the insertion tube 17 and pins 22 of the handle of the trocar 300 mating with an opening in the proximal end of the internal hub 14. The depth of the insertion tube 17 may be adjusted by rotating the trocar 300, which, in turn, will rotate the internal hub 14. Once the insertion tube 17 is set to a desired depth, the needle 300a is used to pierce the eye in the pars plana region, with the insertion tube 17 following the needle 300a through the outer layers of the eye 200 until the end of the insertion tube 17 is in the vitreous chamber 202. Once the insertion tube 17 is fully inserted and the distal end of the cylindrical shell 10 of the port 100 rests against the outer surface of the eye 200, the trocar 300 and needle 300a are removed from the port 100. An infusion cannula assembly 400, having a cannula hub, body or handle 24 and an infusion cannula 25, which is attached to a vitrectomy machine through an infusion tube 23, is inserted into the port 100 with the infusion cannula 25 extending through the insertion tube 17 of the port 100. The surgeon visually checks the depth of the tip of the cannula 25 extending from the insertion tube 17, and if deemed necessary, the insertion tube 17 depth is adjusted by rotating the cannula handle 24, which is mated with the internal hub 14, to rotate the internal hub 14, thereby adjusting the insertion tube 17 depth. Once the infusion cannula 25 is fully inserted into the port 100, the vitrectomy machine is used to infuse fluid into the eye 200 as needed to maintain ocular pressure during the vitrectomy and the procedure requiring the vitrectomy.

In some cases, multiple cannula systems 100 may be used for a pars plana vitrectomy. The ports 100 may also be used for draining the vitreous fluid, as well as insertion of tools, such as a cutter or a light. These secondary ports 100 will be inserted into the eye and adjusted as discussed above.

It is to be understood that the infusion cannula system for pars plana vitrectomy is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A port for an infusion cannula system for pars plana vitrectomy, the port comprising:
    an external cylindrical shell having:
        a proximal end and a distal end, the cylindrical shell defining a bore extending from the proximal end to the distal end; and
        at least one internal thread defined in the bore;
    an internal hub rotatable in the bore defined by the cylindrical shell, the hub having:
        a cylindrical body having a proximal end and an insertion tube extending from the cylindrical body opposite the proximal end of the cylindrical body, the hub having a continuous lumen extending through the insertion tube and the proximal end of the cylindrical body, the lumen being dimensioned and configured for insertion of an infusion cannula therethrough;
        a helical channel defined therein extending at least partially along the cylindrical body; and
    at least one external thread defined on the cylindrical body, the at least one external thread engaging the at least one internal thread defined in the cylindrical shell to raise and lower the hub by rotation of the hub in the shell; and
    at least one pin extending through the cylindrical shell into the channel defined in the cylindrical body of the hub, the at least one pin defining a stop limiting rotation of the hub in the shell so that the hub is rotatable through a defined angle less than 360°, the insertion tube extending from the distal end of the cylindrical shell and adapted for insertion through a sclerotomy incision into a vitreous chamber of a patient's eye to a depth adjustable by rotation of the hub in the cylindrical shell, the cylindrical shell remaining stationary against the patient's eye.

2. The port according to claim 1, wherein the hub is rotatable in the cylindrical shell through an angle of 240°.

3. The port according to claim 2, wherein the insertion tube extends from the distal end of the cylindrical shell to a depth between 3 mm and 7 mm.

4. The port according to claim 3, further comprising a pointer extending laterally from the hub above the proximal end of the cylindrical shell.

5. The port according to claim 4, further comprising a calibrated indicia radially spaced on the proximal end of the cylindrical shell, the calibrated indicia corresponding to the depth the insertion tube extends from the distal end of the cylindrical shell.

6. The port according to claim 5, wherein the calibrated indicia includes indicia "3", "5", and "7", corresponding to depths of 3 mm, 5 mm, and 7 mm, respectively, that the insertion tube extends from the distal end of the cylindrical shell.

7. The port according to claim 6, further comprising notches defined in the proximal end of the cylindrical shell at calibrated radial angles between the calibrated indicia corresponding to depths of 4 mm and 6 mm that the insertion tube extends from the distal end of the cylindrical shell.

8. The port according to claim 1, further comprising a plurality of wings extending from the cylindrical shell at spaced radial angles, the wings being adapted for gripping by a surgeon to prevent rotation of the cylindrical shell when the hub is rotated.

9. The port according to claim 8, wherein the plurality of wings consists of three wings.

10. The port according to claim 1, wherein the lumen defined in the hub has an opening defined at the proximal end of the hub dimensioned and configured for receiving a snap fit of pins extending from a trocar handle and pins extending from an infusion cannula body for rotating the hub.

11. An infusion cannula system for pars plana vitrectomy, comprising:
a port having:
an external cylindrical shell adapted for placement on a patient's eye over a sclerotomy incision;
an internal hub rotatable in the external cylindrical shell through a predefined arc, wherein the internal hub has a proximal face having an opening to a lumen defined therein; and
an insertion tube extending from the hub and adapted for insertion through the sclerotomy incision into a vitreous chamber in the patient's eye, the insertion tube being insertable in the patient's eye through a range of depths controlled by rotation of the hub in the external cylindrical shell in the predefined arc, the hub and the insertion tube having a continuous lumen extending therethrough; and
an infusion cannula assembly having:
an infusion cannula having a cannula body and a cannula tube extending from the cannula body, the cannula tube being insertable through the lumen of the internal hub defined through the internal hub and the insertion tube and into the vitreous chamber to a depth defined by the insertion tube;
the cannula body having pins projecting therefrom on diametrically opposite sides of the cannula tube, the pins forming a snap fit with the opening to the lumen in the proximal face of the internal hub, whereby the cannula body releasably interlocks with the internal hub to permit adjustment of infusion cannula depth in the vitreous chamber after installation of the infusion cannula; and
an infusion tube having a first end attached to the cannula body and a second end adapted for attachment to a vitrectomy machine.

12. The infusion cannula system according to claim 11, wherein said external cylindrical shell further comprises a plurality of wings extending radially from the external cylindrical shell, the wings being adapted for manipulation by a surgeon to hold said external cylindrical shell stationary when said internal hub is being rotated.

13. The infusion cannula system according to claim 11, wherein:
said internal hub further comprises a depth indicator pointer extending radially therefrom; and
said external cylindrical shell further comprises radially spaced calibrated depth indicia corresponding to the depth the insertion tube is extended from said external cylindrical shell.

14. The infusion cannula system according to claim 11, wherein said insertion tube, and said infusion cannula tube when fully inserted in the insertion tube, are extendable into the vitreous chamber to a depth between 3 mm and 7 mm.

15. The infusion cannula system according to claim 11, wherein said cannula body further comprises diametrically opposite wings extending radially from said cannula body for rotating said internal hub when said cannula body is interlocked with said internal hub.

16. The infusion cannula system according to claim 11, further comprising a trocar having a trocar handle and a trocar needle extending therefrom, the trocar for installing said port.

17. The infusion cannula system according to claim 16, wherein said trocar further comprises a pair of pins projecting from the trocar handle on opposite sides of the trocar needle, the pins forming a snap fit with the opening to the lumen in the proximal face of said internal hub, whereby said trocar handle releasably interlocks with said internal hub to permit adjustment of infusion cannula depth in the vitreous chamber before installation of said infusion cannula.

* * * * *